(12) United States Patent
Chen et al.

(10) Patent No.: US 10,568,324 B2
(45) Date of Patent: Feb. 25, 2020

(54) AGRICULTURAL AND HORTICULTURAL MATERIAL, AND PLANT CULTIVATION METHOD WHICH PROMOTE COLORING IN FRUIT

(71) Applicant: AJINOMOTO CO., INC., Tokyo (JP)

(72) Inventors: Yang Chen, Kanagawa (JP); Daisuke Igarashi, Kanagawa (JP); Shunji Suzuki, Yamanashi (JP)

(73) Assignee: AJINOMOTO CO., INC., Tokyo (JP)

( * ) Notice: Subject to any disclaimer, the term of this patent is extended or adjusted under 35 U.S.C. 154(b) by 79 days.

(21) Appl. No.: 15/892,825

(22) Filed: Feb. 9, 2018

(65) Prior Publication Data

US 2018/0168153 A1 Jun. 21, 2018

Related U.S. Application Data

(63) Continuation of application No. PCT/JP2016/072499, filed on Aug. 1, 2016.

(30) Foreign Application Priority Data

Aug. 11, 2015 (JP) ................................ 2015-158971

(51) Int. Cl.
| | | |
|---|---|---|
| *A01N 37/44* | (2006.01) | |
| *A01G 7/06* | (2006.01) | |
| *A01N 37/42* | (2006.01) | |
| *A01N 25/02* | (2006.01) | |
| *A01G 22/05* | (2018.01) | |
| *A01G 17/00* | (2006.01) | |
| *A01G 17/02* | (2006.01) | |
| *A01N 63/02* | (2006.01) | |

(52) U.S. Cl.
CPC ............... *A01N 37/44* (2013.01); *A01G 7/06* (2013.01); *A01G 17/005* (2013.01); *A01G 17/02* (2013.01); *A01G 22/05* (2018.02); *A01N 25/02* (2013.01); *A01N 37/42* (2013.01); *A01N 63/02* (2013.01)

(58) Field of Classification Search
None
See application file for complete search history.

(56) References Cited

U.S. PATENT DOCUMENTS

| 9,173,407 B2 | 11/2015 | Igarashi et al. |
|---|---|---|
| 2008/0293574 A1 | 11/2008 | Venburg et al. |
| 2009/0124503 A1 | 5/2009 | Venburg et al. |
| 2017/0000122 A1 | 1/2017 | Lang et al. |

FOREIGN PATENT DOCUMENTS

| CL | 2008000248 A1 | 10/2008 | |
|---|---|---|---|
| CL | 2008003567 A1 | 1/2010 | |
| CN | 101352165 A | * 1/2009 | ............. A01N 37/12 |
| JP | 62-215503 A | 9/1987 | |
| JP | 02-270802 A | 11/1990 | |
| JP | 04-063599 A | 2/1992 | |
| JP | 2003-048803 A | 2/2003 | |
| JP | 2012-010694 A | 1/2012 | |
| JP | 2012-197249 A | 10/2012 | |
| KR | 10-2013-0107406 A | 10/2013 | |

OTHER PUBLICATIONS

Google Patents English machine translation of CN 101352165 A (Jan. 28, 2009) (https://patents.google.com/CN101352165A/en) retrieved on Jun. 23, 2019.*
International Search Report for PCT Patent App. No. PCT/JP2016/072499 (dated Oct. 18, 2016).
Niikawa, T., et al., "Effects of Fertilizer Containing (S)-(+)-Abscisic Acid (S-ABA) on Skin Color of 'Fuyu' Persimmon Fruits Before and After the Onset of Coloring," Hort Res. (Japan) 2014;13(3):267-274, with English translation.
Wu, X.-P., et al., "Effects of Extraneous Source Amino Acid on the Contents of Amino Acid of Tobacco Leaves," Scientia Agricultura Sinica 2004;37(3):357-361, with English translation.
El-Sayed, M. E. A., "Improving Fruit Quality and Marketing of "Crimson Seedless" Grape Using Some Preharvest Treatments," J. Horticultural Sci. & Ornamental Plants 2013;5(3):218-226.
Portu, J., et al., "Changes on grape phenolic composition induced by grapevine foliar applications of phenylalanine and urea," Food Chemistry 2015;180:171-180.
Wasilewska, A., et al., "An Update on Abscisic Acid Signaling in Plants and More," Molecular Plant 2008;1 (2)198-217.
Takos, A. M., et al., "Light-Induced Expression of a MYB Gene Regulates Anthocyanin Biosynthesis in Red Apples," Plant Physiol. 2006;142:1216-1232.
Jeong, S. T., et al., "Effects of plant hormones and shading on the accumulation of anthocyanins and the expression of anthocyanin biosynthetic genes in grape berry skins," Plant Science 2004;167:247-252.
International Preliminary Report on Patentability for PCT Patent App. No. PCT/JP2016/072499 (dated Feb. 22, 2018).
Extended European Search Report from European Patent App. No. 16835010.6 (dated Feb. 7, 2019).
Database CA [Online], Chemical Abstracts Service, Columbus, Ohio, US; Tian, Xiaoyan et al., XP002788265, CN 101352165 A (Jan. 28, 2009), Accession No. 150:207715 CA; retrieved from the internet Jan. 23, 2019.
Database WPI, Week 199215, Thomson Scientific, London, GB; AN 1992-120158, XP002788266, JP H04-063599 A , (Feb. 28, 1992); retrieved from the Internet Jan. 23, 2019.
Servettaz, D., et al., "The Effect of Benzyladenine on Anthocyanin Accumulation in Excised Sunflower Cotyledons," Plant Sci. Lett. 1975;4:361-368.

(Continued)

*Primary Examiner* — Brian J Davis
(74) *Attorney, Agent, or Firm* — Cermak Nakajima & McGowen; Shelly Guest Cermak

(57) ABSTRACT

Coloring of fruits is promoted by applying a one or more the amino acids leucine, isoleucine, and/or phenylalanine, in combination with abscisic acid to a fruit plant, such as those of the genus Vitaceae or Rosaceae. The amino acid(s) and abscisic acid may be present in a solution(s) having concentrations of 0.2 mM to 100 mM and 0.1 μM to 10 mM, respectively.

10 Claims, 6 Drawing Sheets

(56) References Cited

OTHER PUBLICATIONS

Kayesh, E., et al., "Fruit skin color and the role anthocyanin," Ada Physiol. Plant 2013;35:2879-2890.
Office Action from corresponding Chilean Patent App. No. 201800373 (dated Jun. 6, 2019).

* cited by examiner

AGRICULTURAL AND HORTICULTURAL MATERIAL, AND PLANT CULTIVATION METHOD WHICH PROMOTE COLORING IN FRUIT

This application is a Continuation of, and claims priority under 35 U.S.C. § 120 to International Application PCT/JP2016/072499, filed Aug. 1, 2016, and claims priority therethrough under 35 U.S.C. § 119 to Japanese Patent Application No. 2015-158971, filed Aug. 11, 2015, the entirety of which is incorporated by reference herein.

BACKGROUND OF THE INVENTION

Field of the Invention

The present invention relates to an agricultural or horticultural material and a method for cultivating a plant. More precisely, the present invention relates to an agricultural or horticultural material that can promote the coloring of fruits, and the use of this material in a method for promoting the coloring of fruits.

Brief Description of the Related Art

In order to improve the growth and quality of fruit crops, chemical fertilizers, plant hormones, reflective sheets, and so forth have been used, as well as the physical turning of the fruit and so forth. However, problems still remain concerning the environmental influences, effectiveness, secondary negative influences, workload, and cost. Amino acids can be used as ingredients in inexpensive agricultural or horticultural compositions, and have been shown to have fewer negative influences on the environment. For example, proline has been used as an active ingredient in a flower bud sprouting promoter (Japanese Patent Laid-open (Kokai) No. 2003-48803), the branched chain amino acids valine and leucine have been used to impart high-temperature tolerance to a plant (Japanese Patent Laid-open (Kokai) No. 2012-197249), 18 different amino acids have been used in a liquefied fertilizer composition to promote plant growth (South Korean Patent Laid-open No. 2013-107406), amino acid or nucleic acid fermentation by-products have been used in agents for enhancing plant allelopathy effect and/or phytoalexin production (Japanese Patent Laid-open (Kokai) No. 2012-10694), and so forth. It has also been reported that hydroponics of tobacco plants in an aqueous solution containing glutamic acid, aspartic acid, and phenylalanine result in increased content of amino acids, chlorophyll, and carotenoids in leaves (Wu, X-P. et al., Scientia Agricultura Sinica, 2004, 37(3):357-361).

As described above, techniques of using amino acids for agricultural or horticultural purposes are known. It has also been reported that the sprinkling of phenylalanine can promote grape color (El-Sayed et al., Journal of Horticultural Science & Ornamental Plants, 2013, 5(3):218-226; Portu et al., Food Chemistry, 2015, 180:171-180), although this effect is insufficient for most purposes.

Abscisic acid is a kind of plant hormone, and it is known to participate in dormancy, break dormancy, opening and closing of stomata, growth inhibition, growth suppression, and so forth. In agriculture, abscisic acid has been reported to promote the growth and coloring of fruits, and so forth, for example, it can promote the coloring of grape, persimmon, and apple (Wasilewska et al., Mol Plant, 2008, 1(2): 198-217; Niikawa et al., Horticultural Research (Japan), 2014, 13(3):267-274; Takos et al., Plant Physiol., 2006, 142:1216-1232; Jeong et al. Plant Science, 2004, 167:247-252). However, abscisic acid is expensive, and therefore, not practical for obtaining sufficient color promotion. Also, abscisic acid's promotion of coloring is not synchronized with the accumulation of saccharides or reduction of acids, and may induce the falling of leaves, depending on the application concentration thereof or environment.

SUMMARY OF THE INVENTION

It is one aspect of the present invention to provide a method for promoting the coloring of fruits, and an agricultural or horticultural material that can promote the coloring of fruits.

If a specific amino acid and abscisic acid are applied to a fruit plant in combination, the anthocyanin content of the fruit can be markedly increased as compared with that obtained when either the abscisic acid or the amino acid alone are applied to the fruit plant.

It is aspect of the present invention to provide a method for promoting coloring of a fruit, the method comprising applying abscisic acid and an amino acid selected from the group consisting of leucine, isoleucine, phenylalanine, and combinations thereof to a fruit plant.

It is further aspect of the present invention to provide a method as described above, wherein said applying comprises applying a solution comprising the amino acid(s) and abscisic acid, or applying an amino acid solution and an abscisic acid solution, wherein the concentration of the amino acid(s) is 0.2 mM to 100 mM, and wherein the concentration of abscisic acid is 0.1 µM to 10 mM.

It is further aspect of the present invention to provide a method as described above, wherein the amino acid(s) is/are L-amino acid(s).

It is further aspect of the present invention to provide a method as described above, wherein the fruit plant bears a fruit containing anthocyanin.

It is further aspect of the present invention to provide a method as described above, wherein the fruit plant is selected from the group consisting of Vitaceae and Rosaceae.

It is further aspect of the present invention to provide a method as described above, wherein the fruit plant bears a fruit selected from the group consisting of grape, apple, peach, cherry, and strawberry.

It is further aspect of the present invention to provide a method as described above, wherein the amino acid(s) is/are present in a solution comprising a purified product of the amino acid(s), a fermentation broth or fermentation by-product of the amino acid(s), or a fractionation product thereof containing the amino acid(s).

It is further aspect of the present invention to provide a method as described above, wherein said applying comprises sprinkling the amino acid(s) and abscisic acid onto a leaf, trunk, stem, fruit surface, or rhizosphere of the fruit plant.

It is further aspect of the present invention to provide a method, the method comprising applying abscisic acid and an amino acid selected from the group consisting of leucine, isoleucine, phenylalanine, and combinations thereof to a fruit plant; and collecting a fruit from the fruit plant.

It is further aspect of the present invention to provide a method as described above, wherein said applying comprises applying a solution comprising the amino acid(s) and abscisic, or applying an amino acid solution and an abscisic acid solution, wherein the concentration of the amino acid(s)

is 0.2 mM to 100 mM, and wherein the concentration of abscisic acid is 0.1 µM to 10 mM.

It is further aspect of the present invention to provide an agricultural or horticultural material comprising abscisic acid and an amino acid selected from the group consisting of leucine, isoleucine, phenylalanine, and combinations thereof as active ingredients.

It is further aspect of the present invention to provide a material as described above, wherein the amino acid(s) is/are in a solution having a concentration of 0.2 mM to 100 mM, and the abscisic acid is in a solution having a concentration of 0.1 µM to 10 mM.

DETAILED DESCRIPTION OF THE EXEMPLARY EMBODIMENTS

Figure 1:
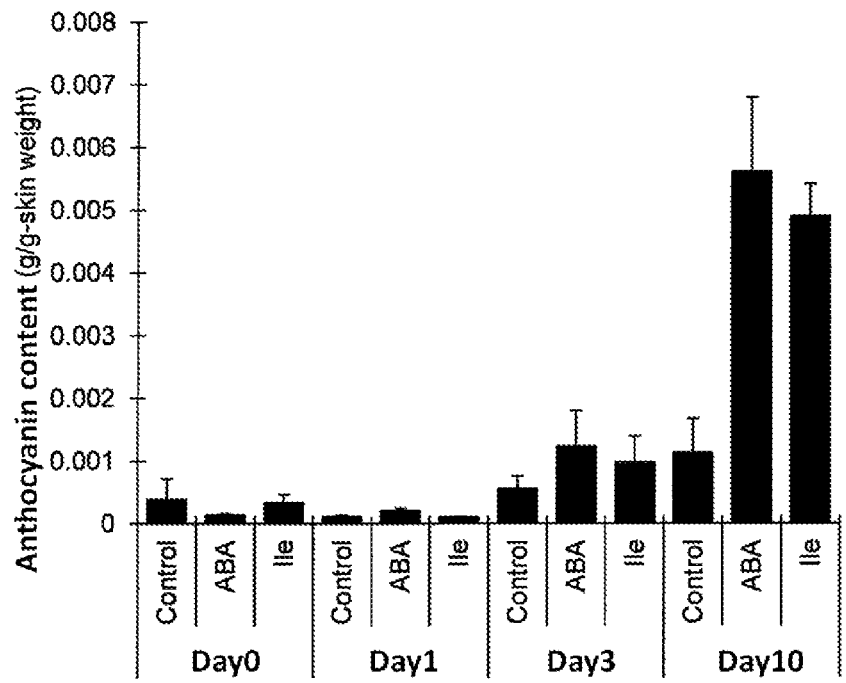
FIG. 1 shows a graph showing the anthocyanin content of grape berries, that is the fruits of a grape plant, on which isoleucine was sprinkled.
Figure 2:
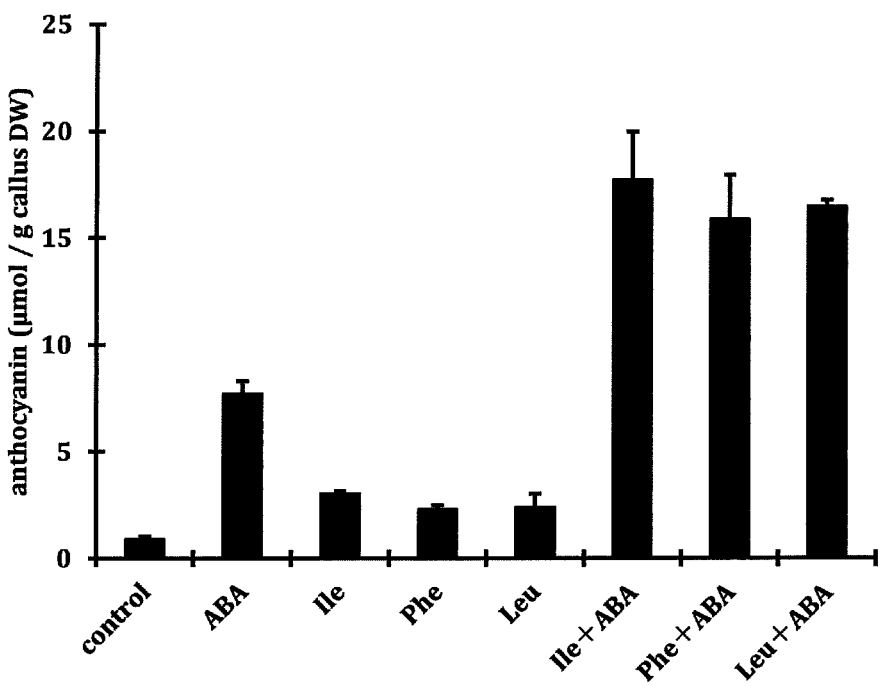
FIG. 2 shows a graph showing the anthocyanin content of grape calluses treated with an amino acid and/or abscisic acid. The vertical axis indicates the amount of anthocyanin (µmol/g callus dry weight, the same is shown in FIGS. 3 to 7). ABA, Ile, Phe, and Leu represent abscisic acid, isoleucine, phenylalanine, and leucine, respectively. The term "control" indicates the result of the control experiment. The symbol "+" indicates combined use.
Figure 3:
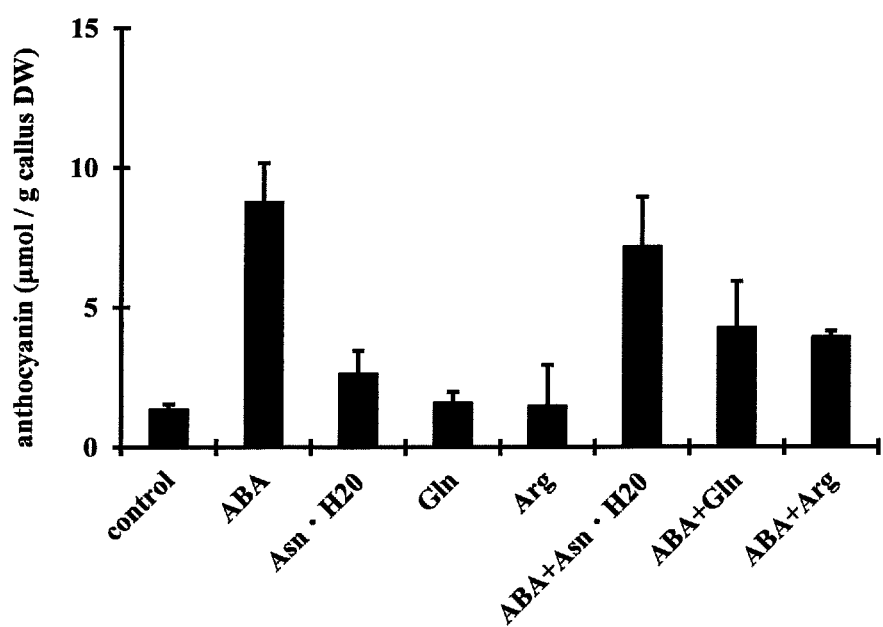
FIG. 3 shows a graph showing the anthocyanin content of grape calluses treated with an amino acid and/or abscisic acid. Asn, Gln, and Arg represent asparagine, glutamine, and arginine, respectively.
Figure 4:
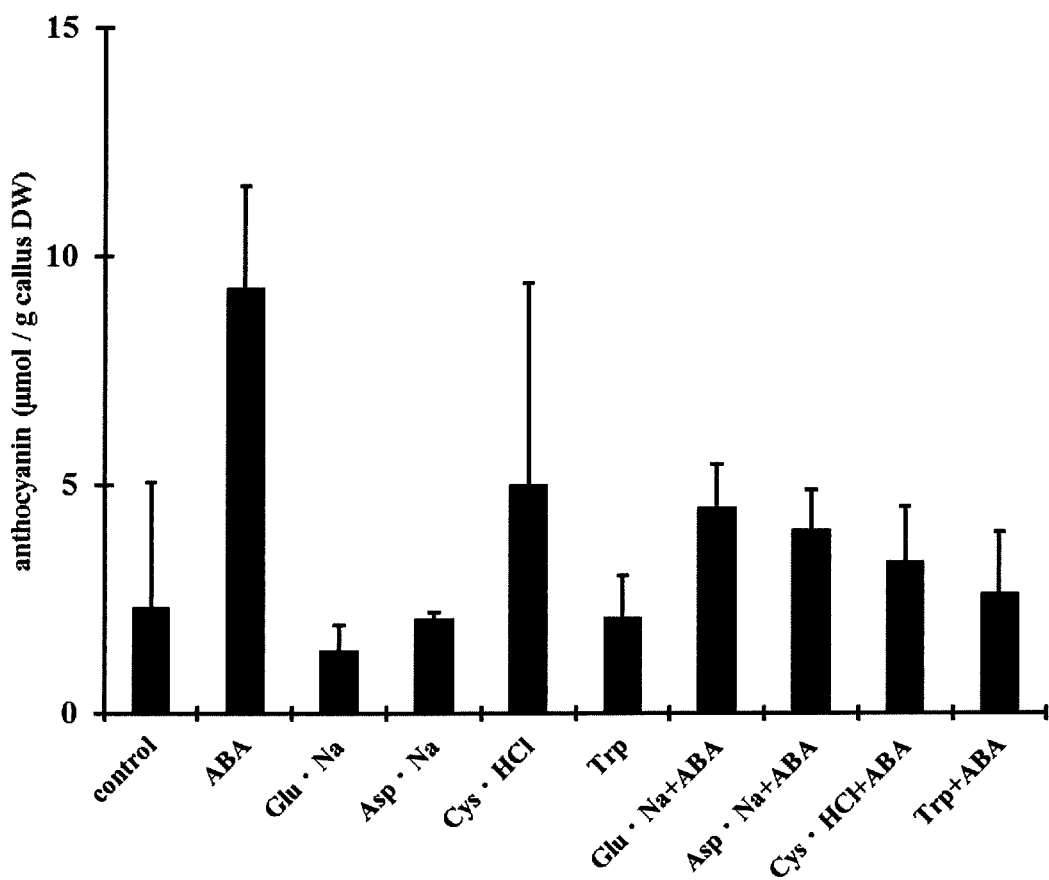
FIG. 4 shows a graph showing the anthocyanin content of grape calluses treated with an amino acid and/or abscisic acid. Glu, Asp, Cys, and Trp represent glutamic acid, aspartic acid, cysteine, and tryptophan, respectively.
Figure 5:
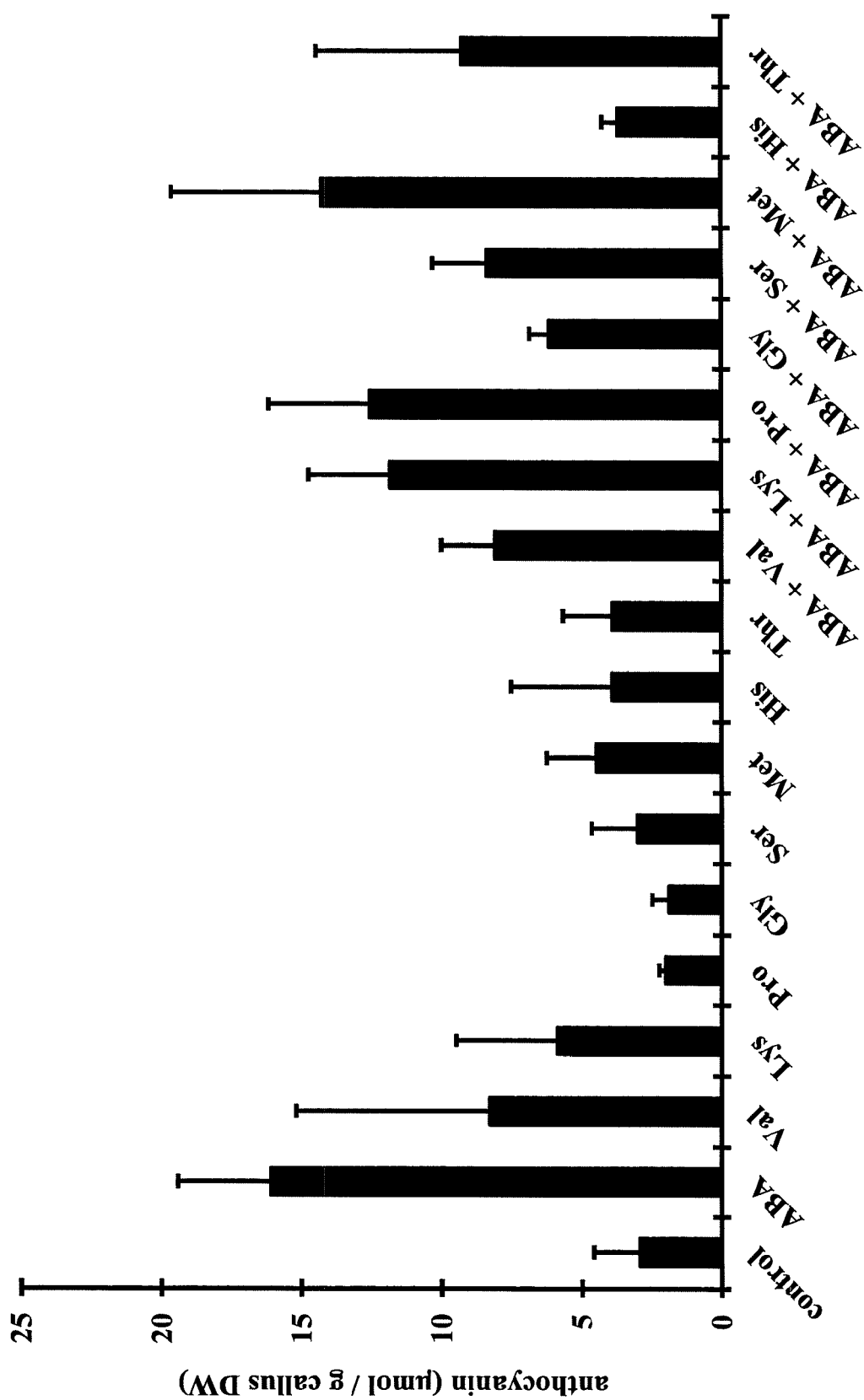
FIG. 5 shows a graph showing the anthocyanin content of grape calluses treated with an amino acid and/or abscisic acid. Val, Lys, Pro, Gly, Ser, Met, His, and Thr represent valine, lysine, proline, glycine, serine, methionine, histidine, and threonine, respectively.

The present invention describes a method for cultivating a fruit plant by applying abscisic acid and the amino acid(s) leucine, isoleucine, and/or phenylalanine to the fruit plant.

The present invention also describes a method for producing a fruit by applying abscisic acid and the amino acid(s) leucine, isoleucine, and/or phenylalanine to a fruit plant, and collecting a fruit from the fruit plant.

The present invention also describes a method for promoting coloring of a fruit by applying abscisic acid and the amino acid(s) leucine, isoleucine, and/or phenylalanine to a fruit plant.

Although the fruit plant is not particularly limited so long as it is a fruit plant that bears a fruit that colors, and a fruit plant that bears a fruit containing an anthocyanin is a particular example. The anthocyanin may include one type of anthocyanin, or two or more types of anthocyanins. The phrase "fruit containing an anthocyanin" can mean a fruit, the color of which is characterized by the anthocyanin, or a fruit in which the anthocyanin is the primary coloring matter of the fruit. The fruit containing an anthocyanin may be a fruit in which the anthocyanin is present in only the pericarp (skin) or the sarcocarp (flesh) of the fruit, or a fruit in which the anthocyanin is present in both of the pericarp and sarcocarp. Therefore, the term "coloring of a fruit" can mean the coloring of either of the pericarp or sarcocarp, or both. The term "fruit plant" can include both an arborous plant and an herb plant. The type of the anthocyanin is not particularly limited, and examples can include cyanidin-3-glucoside, malvidin-3-glucoside, delphinidin-3-glucoside, petunidin-3-glucoside, and so forth. Specific examples of the fruit plant can include fruit plants belonging to the family Vitaceae or Rosaceae. More specific examples include grape, apple, peach, cherry, strawberry plants, and so forth. Although the varieties of these fruit plants are not particularly limited, examples can include, for example, grapes including Cabernet Sauvignon, Merlot, Tempranillo, Pinot Noir, Syrah, Muscat Bailey A, Kyoho, Pione, Delaware, clone 21, Crimson seedless, Flame seedless, Red globe, and so forth; apples including Tsugaru, Fuji, and so forth; peach including Hakuho, Akatsuki, KawaNakajima white peach, Nikkawa Hakuho, and so forth; cherries including Jabore, Satonishiki, Takasago, Napoleon, Benishuho, and so forth; and strawberries including Amaou, Tochiotome, Sagahonoka, Diamond Berry, Sakihime, and so forth. The fruit plant as described herein may include one kind of fruit plant, or two or more kinds of fruit plants.

As described in the examples herein, the abscisic acid activity of increasing anthocyanin content in grapes is increased when abscisic acid is used in combination with the amino acid(s) as described herein.

The amino acid may be any of leucine, isoleucine, and/or phenylalanine, or any arbitrary mixture of two or three of these. In a mixture, quantitative ratios of the amino acids may be arbitrarily determined. The amino acids can be L-amino acids. The amino acids may be in the form of a salt or derivative thereof. The amino acid may be purified or partially purified, or may consist of a culture product, such as a fermentation broth, or fermentation by-product containing the amino acid, or a fractionation product thereof containing the amino acid, so long as the effect of the method as described herein is not degraded. The amino acid may also be a protein decomposition product.

Although abscisic acid may exist as several kinds of isomers, the naturally occurring type abscisic acid ((S)-(+)-abscisic acid) is particular example. Abscisic acid may be a salt thereof or a derivative thereof such as trifluoromethylated abscisic acid. The abscisic acid may also include an abscisic acid agonist having abscisic acid activity, such as pyrabactin, or an abscisic acid decomposition inhibitor such as P450 inhibitor. Abscisic acid can be obtained by, for example, fermentation or chemical synthesis.

The amino acid and abscisic acid can be applied as a solution to a fruit plant. The concentration of the amino acid at the time of the application is usually 0.2 mM to 100 mM, 0.5 mM to 20 mM, 1 mM to 10 mM, or 2 mM to 10 mM. When the amino acid includes two or three kinds of amino acids, these concentration ranges can be the total concentration of the amino acids. The concentration of abscisic acid at the time of the application is usually 0.1 μM to 10 mM, 1 μM to 5 mM, 10 μM to 1 mM, or 100 μM to 1 mM.

The amino acid and abscisic acid may be in one solution together, or in separate solutions. In the latter case, both the solution containing the amino acid and the solution containing abscisic acid are applied to the fruit plant.

The solution(s) of amino acid and abscisic acid can be applied to a leaf, trunk, stem, fruit surface, or rhizosphere, of a fruit plant. The solution(s) of amino acid and abscisic acid may be applied to two or more of these plant parts. The solution(s) of the amino acid and abscisic acid may be applied to the whole or a part of any of these plant parts. For example, when the solution(s) is applied to a leaf, it may be applied to only a front or back surface of the leaf, or may be applied to both sides. When the solution(s) of amino acid and abscisic acid is applied to a fruit, it may be applied to the entire fruit surface, or only a part of a fruit surface, for example, only the outside of a bunch when the fruit forms a bunch. The phrase "application to a fruit plant" can include application of the solution(s) of amino acid and abscisic acid to soil, so long as the amino acid and abscisic acid are able to reach at least the rhizosphere. Examples of the application method can include sprinkling to soil surface, irrigation into soil, plowing into soil, sprinkling or spreading on leaf surface or fruit of the fruit plant, addition to hydroponic solution, and so forth. Among these, sprinkling on a leaf surface or fruit is a particular example. The phrase "sprinkling on a leaf surface" can mean that sprinkling on at least leaf surface is sufficient, and the solution may be sprinkled on another part in addition to a leaf surface. The same shall apply to a fruit.

Although the sprinkling amount of the solution(s) of amino acid and abscisic acid is not particularly limited, it can be 60 g/ha to 30,000 g/ha, 150 g/ha to 600 g/ha, 300 g/ha to 3,000 g/ha, 600 g/ha to 3,000 g/ha, in terms of the amount of amino acid. When the amino acid includes two or three kinds of amino acids, the concentration can mean the total concentration of the amino acids.

The amount of abscisic acid can be 0.05 g/ha to 5,000 g/ha, 0.5 g/ha to 2,000 g/ha, 5 g/ha to 2,000 g/ha, or 10 g/ha to 2,000 g/ha.

The ratio of the amounts of the amino acid(s) and abscisic acid is not particularly limited.

As for when the solution(s) of amino acid and abscisic acid should be applied, it can be applied to a fruit plant after the fruit plant has born a fruit. After bearing fruit, the solution(s) of amino acid and abscisic acid can be applied before or after the coloring of the fruit or both before and after. Especially for grape, the solution(s) of amino acid and abscisic acid can be applied during the veraison period. The number of times of the application is not particularly limited, and the solution(s) of amino acid and abscisic acid may be applied once or two or more times. When applying separate solutions of amino acid and abscisic acid, the solutions may be applied simultaneously or separately. When these solutions are separately applied, both solutions can be applied within seven days.

When the solution(s) of amino acid and abscisic acid is/are sprinkled, the sprinkling method is not particularly limited, but it can be that the solution(s) as part of an agricultural or horticultural material can be spread over the whole terrestrial part of a plant including a stem, leaf, and fruit, such as over a leaf surface and/or fruit. When the solution(s) is manually sprinkled, the sprinkling can be performed so that a spray nozzle applies the solution(s) as a part of an agricultural or horticultural material to the front or back surface of a leaf. When a boom sprayer is used, the sprinkling volume of the solution(s) can be 100 L or larger, 200 to 3,000 L, or 300 to 2,000 L, per ha. A so-called electrostatic spraying machine or electrostatic spraying nozzle can be used, which promotes adhesion of the liquid sprayed onto the plant bodies by using static electricity.

When the solution(s) of amino acid and abscisic acid is sprinkled on a leaf surface and/or fruit, it may be sprinkled as a mixture with a fertilizer for foliar applications usually used in agriculture so long as the effect of the method as described herein is not degraded.

When a plant is cultivated according to the method as described herein, a basal fertilizer and an additional fertilizer can be applied to the soil in an amount and by a method usually used in the corresponding area depending on the type of the plant.

One embodiment of the present invention as described herein is an agricultural or horticultural material containing a solution(s) of amino acid and abscisic acid.

The agricultural or horticultural material can contain the amino acid(s) leucine, isoleucine, and/or phenylalanine, and abscisic acid as active ingredients. The amino acids and abscisic acid are described herein and these descriptions are applicable for those used in the agricultural or horticultural material. The agricultural or horticultural material may contain the amino acid and abscisic acid in separate materials, or the amino acid and abscisic acid may both be present in the agricultural or horticultural material as a mixture. The form of the agricultural or horticultural material can include, for example, an agricultural or horticultural material containing an amino acid solution and an abscisic acid solution, an agricultural or horticultural material containing a solution containing the amino acid and abscisic acid, an agricultural or horticultural material containing a powdered amino acid, powdered abscisic acid, and a solvent for dissolving them as an optional component, and so forth. When the amino acid and abscisic acid are separate, they may be mixed at the time of use, or they may be separately applied to a fruit plant.

The agricultural or horticultural material may contain one or more other arbitrary ingredients in addition to the aforementioned active ingredients, so long as the effect of the method as described herein is not degraded. Examples of these other arbitrary ingredients can include a stabilizer, carrier, pH adjustor, fertilizer component such as minerals for enhancing effect of fertilizer, agrochemical ingredient, binder, filler, and so forth. As these ingredients, those usually used for agricultural chemicals, fertilizers, and so forth can be used, so long as the effect of the method as described herein is not degraded.

The agricultural or horticultural material may also contain an amino acid other than leucine, isoleucine, and phenylalanine. However, since such other amino acids include those that reduce the fruit coloring-promoting action of abscisic acid, these other amino acids should only be present in small amounts in the agricultural or horticultural material, and such other amino acids may not be present at all in the agricultural or horticultural material. For example, the other amino acids can be present in an amount of 10 mM or lower, or 1 mM or lower, in terms of the concentration at the time of applying the agricultural or horticultural material to a fruit plant.

The dosage form of the agricultural or horticultural material is not particularly limited so long as a solution applicable to a fruit plant can be prepared at the time of use, and the material may be in any form, such as a solution, powder, granule, or emulsion.

As described above, when the agricultural or horticultural material is sprinkled on a plant, it can be sprinkled on a leaf surface and/or fruit. A spreading agent may be added in order to enhance the spreading ability of the agricultural or horticultural material on a leaf surface or fruit. Such ingredients include a surfactant, which may be added in order to enhance the penetration into a plant of isoleucine. Examples of the spreading agent can include, for example, Applauch BI™ (Kao), Mix Power™ (Syngenta Japan), Squash™ (MARUWA Biochemical), and so forth. As the surfactant, nonionic surfactants, anionic surfactants, cationic surfactants, or ampholytic surfactants can be used. Examples can include polyoxyethylene alkyl ethers, polyoxyethylene alkyl aryl ethers, polyoxyethylene fatty acid esters, sorbitan fatty acid esters, polyoxyethylene sorbitan fatty acid esters, oxyethylene polymers, oxypropylene polymers, polyoxyethylene alkyl phosphoric acid esters, fatty acid salts, alkylsulfuric acid ester salts, alkylsulfonic acid salts, alkylarylsulfonic acid salts, alkylphosphoric acid salts, alkylphosphoric acid ester salts, polyoxyethylene alkylsulfuric acid esters, quaternary ammonium salts, oxyalkylamines, lecithin, saponin, and so forth. In addition, gelatin, casein, starch, agar, polyvinyl alcohol, sodium alginate, and so forth can be used as an auxiliary as required.

At the time of use, when the agricultural or horticultural material or a component thereof is in the form of a solid or powder, it may be dissolved or dispersed in a solvent such as water and/or alcohol. Also, when the agricultural or horticultural material or a component thereof is in the form of liquid, it may be diluted with a solvent such as water and/or alcohol. Examples of the alcohol can include ethanol, methanol, isopropyl alcohol, and so forth.

The concentration of leucine, isoleucine, and/or phenylalanine at the time of use of the agricultural or horticultural material is as described herein. The amount of these amino acids in the agricultural or horticultural material is not particularly limited so long as these amino acids are applied as a solution of the prescribed concentration described above at the time of use. The amount of these amino acids in the agricultural or horticultural material can be, for example, 1% by weight or higher, 50% by weight or higher, or 70% by weight or higher, in terms of dry weight, and the amount can be in such a range the harmful effect of impurities such as damage caused by salt can be avoided. Although the agricultural or horticultural material may be distributed in the form of solid or solution, when it is distributed in the form of solution, the concentration thereof can be 0.5 mM to the saturation concentration. The solubility in water of isoleucine is about 0.3 M (40.2 g/L (20° C.), 41.2 g/L (50° C.)), phenylalanine is about 0.2 M (27 g/L (20° C.), 40 g/L (50° C.)), and leucine is about 0.2 M (24 g/L (20° C.), 29 g/L (50° C.)).

The concentration of abscisic acid at the time of use in the agricultural or horticultural material is also as described herein. The amount of abscisic acid in the agricultural or horticultural material is not particularly limited so long as it can be applied as a solution at the prescribed concentration described above at the time of use. When the agricultural or horticultural material is in the form of solution, the concentration of abscisic acid can be 0.5 mM to the saturation concentration.

EXAMPLES

Hereafter, the present invention will be more specifically explained with reference to the following non-limiting examples. In the examples, amino acids are L-amino acids.

Reference Example 1: Effect of Isoleucine on Anthocyanin Content in Grape Cultured Cells (1) Effect of Isoleucine and Various Amino Acids on Coloring of Grape Cultured Cells Cells derived from a European grape cell line (*Vitis vinifera* L.; RIKEN BioResource Center; VR, management number RPC00003) were subcultured on MS agar medium. The subcultured VR calluses (i.e. cell clusters) were each transferred to MS agar medium containing 5 mM of each amino acid solution, and cultured. As a positive control, 100 µM abscisic acid (ABA) was added, which is a known color-promoter. Five days after the transfer, each callus was freeze-dried and ground, and anthocyanin was extracted with a 1% HCl solution in MeOH. The absorbance of the extract was measured at 530 nm, and the content of anthocyanin was quantified by using cyanidin-3-glucoside as a standard. The relative value of the content of anthocyanin that had accumulated in the callus of each amino acid treatment group was determined based on the content of anthocyanin extracted from the callus of the positive control treatment group, which was taken as 100%.

The results are shown in Table 1. The callus treated with isoleucine (Ile) showed the highest anthocyanin content.

TABLE 1

Analysis of anthocyanin contents in grape calluses treated with various amino acids

| Amino acid | Pro | Ile | Asp | Glu | Ser | Asn | Gln | Gly | His | Arg |
|---|---|---|---|---|---|---|---|---|---|---|
| Relative content of anthocyanin | 27% | 76% | 11% | 4% | 38% | 38% | 18% | 23% | 29% | 9% |

| Amino acid | Val | Met | Ala | Trp | Phe | Cys | Leu | Thr | Lys | Try |
|---|---|---|---|---|---|---|---|---|---|---|
| Relative content of anthocyanin | 6% | 42% | 7% | 4% | 40% | 6% | 30% | 35% | 15% | 0% |

(2) Effect of Isoleucine on Coloring of Grape Berries

Cabernet Sauvignon grape plants that had been cultivated in a test farm and had entered into the veraison period were chosen for this experiment. Eight bunches of grapes on each of two grape plants, 16 bunches of grapes in total, were selected for each test group. On each bunch of grapes, about 6.25 mL of 0.1% Applauch BI (Kao, control), 1 g/L of abscisic acid (ABA)+0.1% Applauch BI (positive control), or 10 mM isoleucine (Ile)+0.1% Applauch BI was sprinkled. As samples, 4 bunches for each test group were collected 4 times. Anthocyanin present in the pericarps was extracted with a mixed solution of water and acetone (1:2), and the anthocyanin content was measured in the same manner as described above. The results are shown in FIG. 1. The data shows that, if grape berries are treated with Ile, the anthocyanin content in pericarps is increased.

As described above, a correlation between the coloring-promoting effect observed for the grape cultured cells and the coloring-promoting effect for grape berries on trees was demonstrated.

Example 1: Evaluation of Coloring of Grape Provided by Amino Acid Treatment

Cells derived from a grape cell line (Vitis vinifera L.; RIKEN BioResource Center; VR, management number RPC00003) were subcultured on MS agar medium. The VR calluses were each transferred to MS agar medium containing 5 mM of each amino acid, or 100 μM abscisic acid (ABA), or 5 mM of each amino acid and 100 μM ABA (abscisic acid), and cultured. The culture was performed at 25° C. with 16 hours of light irradiation in one day.

After 5 days, each callus was freeze-dried and ground, and anthocyanin was extracted with a 1% HCl solution in MeOH. The absorbance of the extract was measured at 530 nm, and the content of anthocyanin was quantified by using cyanidin-3-glucoside as a standard, and shown in the graphs in terms of the content in dry weight (DW) of the callus. The amounts of anthocyanin per 1 g dry weight of callus are shown in FIGS. 2 to 5. When the calluses were treated with a combination of ABA and isoleucine (Ile), phenylalanine (Phe), or leucine (Leu), the anthocyanin content of the calluses markedly increased as compared with that observed with the treatment with ABA alone.

Example 2: Evaluation of Coloring of Grape Provided by Amino Acid Treatment

Cells derived from a grape cell line (Vitis vinifera L.; RIKEN BioResource Center; VR, management number RPC00003) were subcultured on MS agar medium. The VR calluses were each transferred to MS agar medium containing 0 to 5 mM of phenylalanine (Phe) or isoleucine (Ile) in combination with 0 to 100 μM abscisic acid (ABA), and cultured. The culture was performed at 25° C. with 16 hours of light irradiation in one day.

Figure 6:
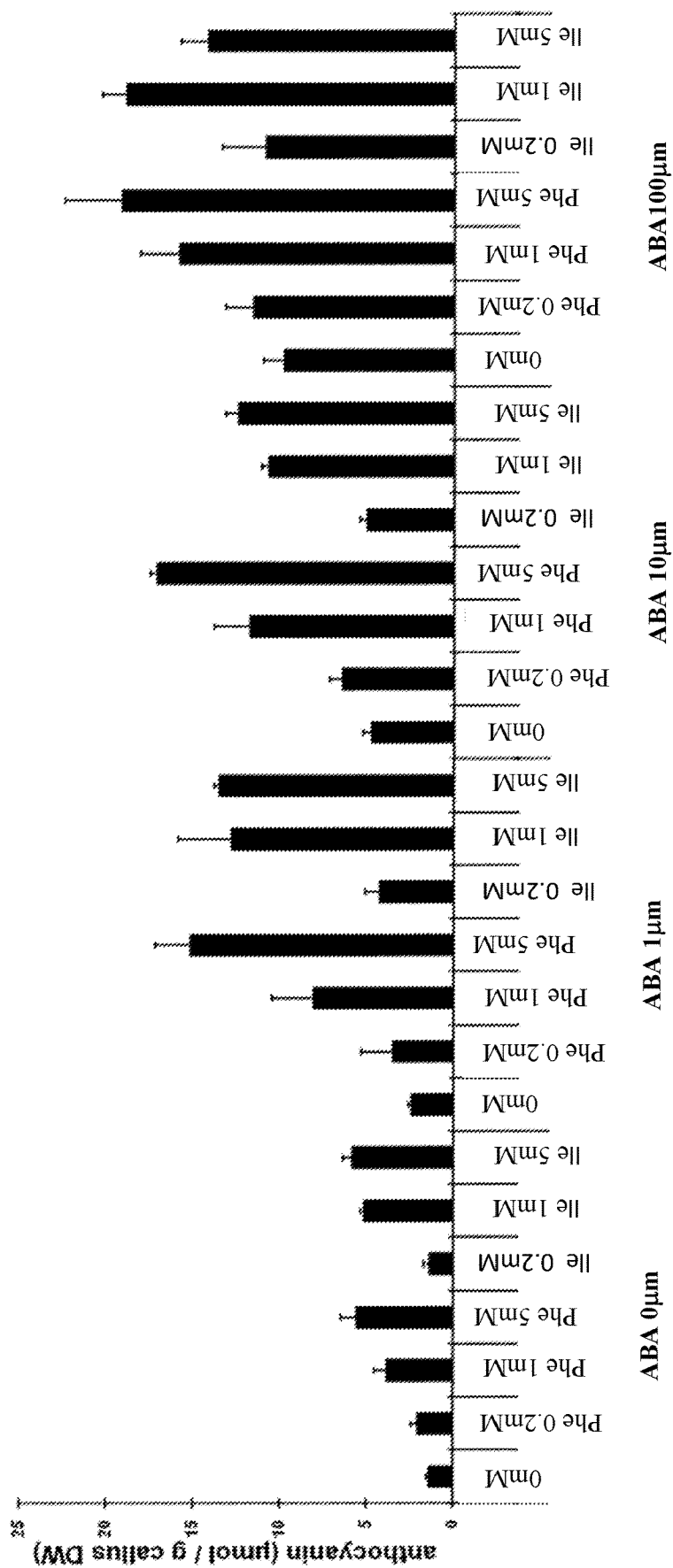
FIG. 6 shows a graph showing the anthocyanin content of grape calluses treated with an amino acid and/or abscisic acid.

After 5 days, each callus was freeze-dried and ground, and anthocyanin was extracted with a 1% HCl solution in MeOH. The absorbance of the extract was measured at 530 nm, and the content of anthocyanin was quantified by using cyanidin-3-glucoside as a standard, and shown in the graph in terms of the content in dry weight (DW) of the callus. The amounts of anthocyanin per 1 g dry weight of callus are shown in FIG. 6. When the calluses were treated with a combination of ABA and isoleucine (Ile) or phenylalanine (Phe), the anthocyanin contents of the calluses markedly increased compared with that observed with the treatment with ABA alone. Furthermore, when the concentration of ABA and the amino acids were increased, the amount of anthocyanin also increased.

Example 3: Evaluation of Coloring of Cabernet Sauvignon Berries Provided by Amino Acid Treatment A 0.3 M sucrose culture solution containing 10 mM phenylalanine (Phe) and 1 mM abscisic acid (ABA) was infiltrated into a filter paper. Cabernet sauvignon berries before entering into the veraison period, that is, at the start of fruit maturation, were placed on the surface of the filter paper, and cultured. The culture was performed at 25° C. with 16 hours of light irradiation in one day.

Figure 7:
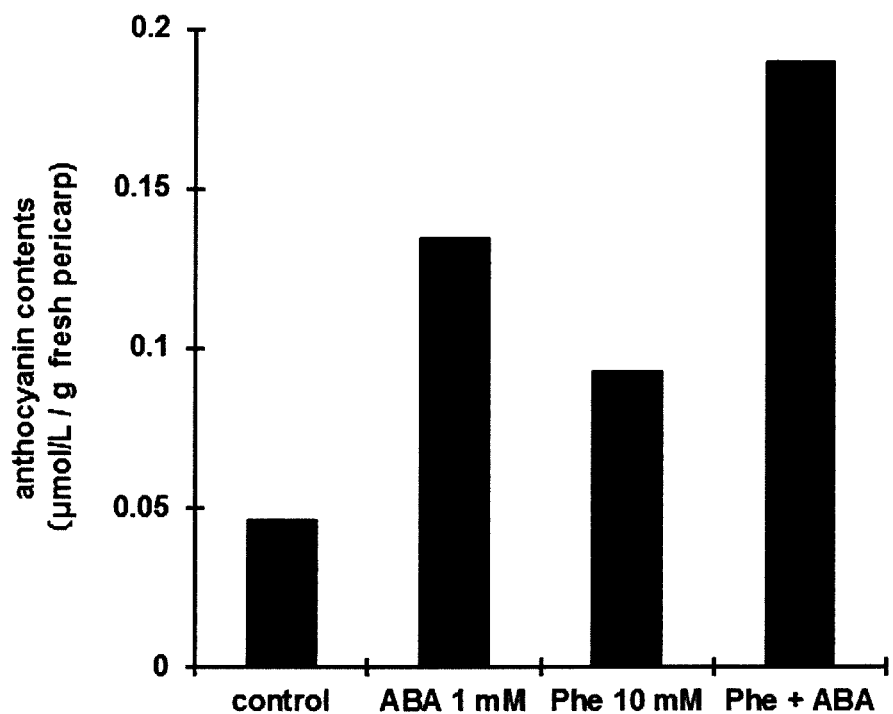
FIG. 7 shows a graph showing the anthocyanin content of grape berries treated with an amino acid and/or abscisic acid.

After 5 days, the pericarps of berries were stripped and ground, and anthocyanin was extracted with a 1% HCl solution in MeOH. The absorbance of the extract was measured at 530 nm, and the content of anthocyanin was quantified by using cyanidin-3-glucoside as a standard, and shown in FIG. 7 in terms of the content in fresh pericarp weight (FW). As a result of the treatment with a combination of ABA and phenylalanine (Phe), the anthocyanin content in the pericarp markedly increased as compared with that observed with the treatment with ABA alone.

As described above, the coloring-promoting effect obtained in the grape cultured cells and the coloring-promoting effect obtained in berries was able to be correlated. On the basis of these results and the result of Reference Example 1, the effect obtained in Examples 1 and 2 can be similarly obtained on fruit plants.

Figure 8:
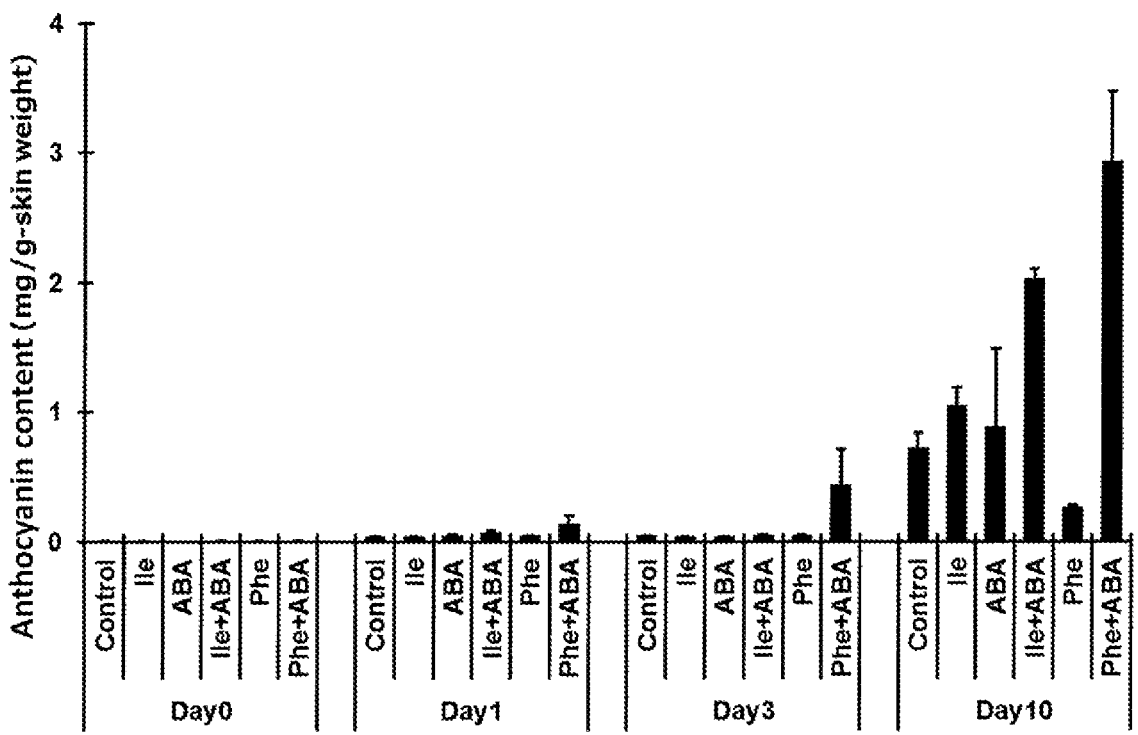
FIG. 8 shows a graph showing the anthocyanin content of grape berries when a bunch was treated with an amino acid and/or abscisic acid. The vertical axis indicates the amount of anthocyanin (mg/g fresh pericarp). Day0, Day 1, Day3, and Day10 indicate results obtained 0, 1, 3, and 10 days after the start of the treatment with an amino acid and/or abscisic acid.

Example 4: Effect of Coloring of Cabernet Sauvignon Berries Provided by Amino Acid Treatment on Fruit Plant Cabernet Sauvignon plants that had been cultivated in a test farm and had entered into the veraison period were chosen for this experiment. The grape plants were divided into three sections, and the experiment was performed in triplicate. Six treatment groups were randomly set for the grape plants in each section. On the fruit bunches of each treatment group, control, 10 mM isoleucine (Ile), 0.1 g/L (378 μM) abscisic acid (ABA), 10 mM isoleucine+0.1 g/L abscisic acid (Ile+ABA), 10 mM phenylalanine (Phe), or 10 mM phenylalanine+0.1 g/L abscisic acid (Phe+ABA), each containing 0.1% Applauch BI (Kao), was sprinkled. The volume of each solution was such that the berries were sufficiently wetted. After 0, 1, 3, and 10 days from the start of the sprinkling, the bunches of each treatment group were harvested, anthocyanin was extracted from the pericarps of the berries (fruit balls) with a mixed solution of water and acetone (1:2), and the anthocyanin content was measured. The results are shown in FIG. 8. When the berries on the fruit plants were treated with the combination of Phe and ABA, the anthocyanin content in the pericarps increased compared with that obtained with the treatment with ABA alone.

INDUSTRIAL APPLICABILITY

By using abscisic acid and a specific amino acid in combination, the coloring of fruits can be further promoted compared with use of abscisic acid or the amino acid alone. According to the present invention, coloring-promoting effect comparable to that obtainable with abscisic acid alone can be attained with a smaller amount of abscisic acid. Amino acids are highly safe, and more inexpensive compared with abscisic acid, and provide fewer side reactions to plants.

The invention claimed is:

1. A method for promoting coloring of a fruit, the method comprising:
applying abscisic acid and an amino acid selected from the group consisting of leucine, isoleucine, and combinations thereof to a fruit plant.
2. The method according to claim 1, wherein said applying comprises:

applying a solution comprising the amino acid(s) and abscisic acid, or applying an amino acid solution and an abscisic acid solution, wherein the concentration of the amino acid(s) is 0.2 mM to 100 mM, and wherein the concentration of abscisic acid is 0.1 µM to 10 mM.

3. The method according to claim 1, wherein the amino acid(s) is/are L-amino acid(s).

4. The method according to claim 1, wherein the fruit plant bears a fruit containing anthocyanin.

5. The method according to claim 1, wherein the fruit plant is selected from the group consisting of Vitaceae and Rosaceae.

6. The method according to claim 5, wherein the fruit plant bears fruit selected from the group consisting of grape, apple, peach, cherry, and strawberry.

7. The method according to claim 1, wherein the amino acid(s) is/are present in a solution comprising:

a fermentation broth or fermentation by-product of the amino acid(s), or a fractionation product thereof containing the amino acid(s).

8. The method according to claim 1, wherein said applying comprises sprinkling the amino acid(s) and abscisic acid onto a leaf, trunk, stem, fruit surface, or rhizosphere of the fruit plant.

9. A method for producing a fruit, the method comprising:

applying abscisic acid and an amino acid selected from the group consisting of leucine, isoleucine, and combinations thereof to a fruit plant; and collecting a fruit from the fruit plant.

10. The method according to claim 9, wherein said applying comprises:

applying a solution comprising the amino acid(s) and abscisic acid, or applying an amino acid solution and an abscisic acid solution, wherein the concentration of the amino acid(s) is 0.2 mM to 100 mM, and wherein the concentration of abscisic acid is 0.1 µM to 10 mM.

* * * * *